US012614557B1

(12) United States Patent
Rubio

(10) Patent No.: US 12,614,557 B1
(45) Date of Patent: Apr. 28, 2026

(54) SYSTEM FOR DETECTING MICROPHONE COMMUNICATIONS MADE UNDER STRESS, AND FOR MITIGATING PROPAGATION OF STRESSED VOICE COMMUNICATIONS

(71) Applicant: TTM Technologies, Inc., Farmingdale, NY (US)

(72) Inventor: Carlton Rubio, Centerport, NY (US)

(73) Assignee: TTM Technologies, Inc., Farmingdale, NY (US)

( * ) Notice: Subject to any disclaimer, the term of this patent is extended or adjusted under 35 U.S.C. 154(b) by 181 days.

(21) Appl. No.: 18/499,478

(22) Filed: Nov. 1, 2023

Related U.S. Application Data

(60) Provisional application No. 63/421,691, filed on Nov. 2, 2022.

(51) Int. Cl.
*G10L 21/01* (2013.01)
*A61B 5/00* (2006.01)
(Continued)

(52) U.S. Cl.
CPC .............. *G10L 21/01* (2013.01); *A61B 5/165* (2013.01); *A61B 5/4803* (2013.01);
(Continued)

(58) Field of Classification Search
CPC ..... G10L 21/01; G10L 15/063; G10L 21/013; G10L 25/63; G10L 25/90;
(Continued)

(56) References Cited

U.S. PATENT DOCUMENTS 5,507,291 A    4/1996   Stirbl
6,151,571 A    11/2000  Pertrushin
(Continued)

FOREIGN PATENT DOCUMENTS

CN    101420665 A    4/2009
CN    101789990 A    7/2010
(Continued)

OTHER PUBLICATIONS

Luig, A Robust Feature Set for Classification of Speech under Stress, Thesis, Institute of Electronic Music and Acoustics, University of Music and Performing Arts, Graz, 2009 (Year: 2009).*
(Continued)

*Primary Examiner* — Bhavesh M Mehta
*Assistant Examiner* — Eunice Lee
(74) *Attorney, Agent, or Firm* — Thomas A. O'Rourke; James Bongiorno; O'Rourke IP Law, PLLC

(57) ABSTRACT

A system to improve pilot voice communication includes: a microphone capturing pilot speech during operational use of an aircraft; and an audio subsystem that stores recordings of the captured pilot speech during different periods of the operational use. A pilot recording selection graphic user interface permits selection by the pilot of recordings made during a low stress period of his/her operational use of the aircraft, and one or more recordings made during a high stress period. A training algorithm analyzes characteristics of the selected recordings made during the low stress period to set a baseline. The training algorithm subsequently analyzes real-time pilot speech to ascertain when its characteristics are increased by a threshold amount over the baseline, which is classified as speech made under stress. The audio system alters and improves the analyzed real-time speech made under stress by converting it to normal-sounding speech, minimizing propagation of stressed speech.

8 Claims, 8 Drawing Sheets

(51) Int. Cl.

| | | |
|---|---|---|
| *A61B 5/16* | (2006.01) |
| *G06F 3/0482* | (2013.01) |
| *G10L 15/06* | (2013.01) |
| *G10L 21/013* | (2013.01) |
| *G10L 25/63* | (2013.01) |
| *G10L 25/90* | (2013.01) |

(52) U.S. Cl.
CPC .......... *G10L 15/063* (2013.01); *G10L 21/013* (2013.01); *G10L 25/63* (2013.01); *G10L 25/90* (2013.01); *A61B 2503/22* (2013.01); *G06F 3/0482* (2013.01); *G10L 2021/0135* (2013.01)

(58) Field of Classification Search
CPC ............. G10L 2021/0135; A61B 5/165; A61B 5/4803; A61B 2503/22; G06F 3/0482
See application file for complete search history.

(56) References Cited

U.S. PATENT DOCUMENTS

| | | | |
|---|---|---|---|
| 7,340,393 B2 | 3/2008 | Mitsuyoshi | |
| 7,580,512 B2 | 8/2009 | Batni | |
| 7,912,720 B1 | 3/2011 | Hakkani-Tur | |
| 8,078,470 B2 | 12/2011 | LeVanOn | |
| 8,204,747 B2 | 6/2012 | Kato | |
| 8,965,770 B2 | 2/2015 | Petrushin | |
| 9,020,822 B2 | 4/2015 | Kalinli-Akbacak | |
| 9,031,293 B2 | 5/2015 | Kalinli-Akbacak | |
| 9,070,357 B1 | 6/2015 | Kennedy | |
| 9,149,236 B2 | 10/2015 | Chun | |
| 9,418,390 B2 | 8/2016 | Chun | |
| 10,096,319 B1 | 10/2018 | Jin | |
| 10,204,642 B2 | 2/2019 | Levanon | |
| 10,276,188 B2 | 4/2019 | Feast | |
| 10,453,453 B2 | 10/2019 | Penilla | |
| 10,496,947 B1 | 12/2019 | Shaburov | |
| 10,599,917 B1 | 3/2020 | Shaburov | |
| 10,734,103 B2 | 8/2020 | Kaneko | |
| 10,783,890 B2 | 9/2020 | Visser | |
| 10,796,176 B2 | 10/2020 | el Kaliouby | |
| 2003/0028384 A1 | 2/2003 | Kemp | |
| 2006/0149428 A1 | 7/2006 | Kim | |
| 2007/0167689 A1 | 7/2007 | Ramadas | |
| 2007/0213981 A1* | 9/2007 | Meyerhoff | G10L 17/26 704/243 |
| 2008/0091515 A1 | 4/2008 | Thieberger | |
| 2012/0116186 A1* | 5/2012 | Shrivastav | G10L 25/48 600/301 |
| 2013/0143185 A1 | 6/2013 | Liu | |
| 2016/0196836 A1 | 7/2016 | Yu | |
| 2020/0027449 A1* | 1/2020 | Lafon | G08G 5/21 |
| 2020/0058208 A1 | 2/2020 | Ogaz | |
| 2021/0390973 A1 | 12/2021 | Raikar | |
| 2023/0005483 A1* | 1/2023 | Garg | G08G 5/53 |
| 2023/0122420 A1* | 4/2023 | Eling | G10L 15/26 704/235 |

FOREIGN PATENT DOCUMENTS

| | | | | |
|---|---|---|---|---|
| CN | 106570496 A | | 4/2017 | |
| CN | 109274819 A | * | 1/2019 | .......... G10L 21/013 |
| CN | 111755027 A | | 10/2020 | |
| DE | 3392884 A1 | | 10/2018 | |
| GB | 2604716 A | * | 9/2022 | ............. G06F 3/167 |

| | | | |
|---|---|---|---|
| JP | 2007041988 A | 2/2007 | |
| JP | 4456537 B2 | 4/2010 | |
| JP | 2013072979 A | 4/2013 | |
| JP | 5394118 B2 | 1/2014 | |
| JP | 2022528691 A | 6/2022 | |
| TW | I221574 B | 10/2004 | |
| WO | WO 2010/148141 | 12/2010 | |
| WO | WO 2020/135194 | 2/2020 | |

OTHER PUBLICATIONS

Fischman, The phase vocoder: theory and practice, Organised Sound, 2.2, 1997 (Year: 1997).*

Yeung, Improving the intelligibility of synthetic speech over the telephone and in noise, Masters Thesis, The University of Edinburgh, 2020 (Year: 2020).*

Frisson et al., CoMediAnnotate: towards more usable multimedia content annotation by adapting the user interface, QPSR of the Numediart Research Program, vol. 3, No. 3, 2010 (Year: 2010).*

Bradford et al., Real-time Sliding Phase Vocoder using a Commodity GPU, Proceedings of ICMC, University of Huddersfield and ICMA, 2011 (Year: 2011).*

Vijay P. Patil, Krishna Kant Nayak, and Manish Saxena, "Voice Stress Detection," International Journal of Electrical, Electronics and Computer Engineering, 148-154 (2013).

P. Rajasekaran, G. Doddington, and Joseph Picone, "Recognition of Speech Under Stress and in Noise," ICASSP'86. IEEE International Conference on Acoustics, Speech, and Signal Processing, vol. 11, IEEE, 1986.

Sondhi, Savita, et al., "Vocal Indicators of Emotional Stress," International Journal of Computer Applications, 38-43, (2015).

Raul Fernandez and Rosalind W. Picard, "Modeling Drivers' Speech Under Stress," Speech Communication, 145-159 (2003).

Pisanski, Katarzyna, Jordan Raine, and David Reby, "Individual Differences in Human Voice Pitch are Preserved from Speech to Screams, Roars and Pain Cries," Royal Society Open Science, 191642 (2020).

Alice Baird, et al., "An evaluation of speech-based recognition of emotional and physiological markers of stress," Frontiers in Computer Science 3 (2021).

Dismukes, R., Timothy E. Goldsmith, and Janeen A. Kochan, "Effects of Acute Stress on Aircrew Performance: Literature Review and Analysis of Operational Aspects," (2015).

Lee, Kyongsun. "Effects of Flight Factors on Pilot Performance, Workload, and Stress at Final Approach to Landing Phase of Flight." (2010).

Hagmüller, Martin, Erhard Rank, and Gernot Kubin. "Evaluation of the human voice for indications of workload-induced stress in the aviation environment." EEC Note 18.06 (2006).

Protopapas, Athanassios, and Philip Lieberman. "Fundamental frequency of phonation and perceived emotional stress." The Journal of the Acoustical Society of America 101.4 (1997): 2267-2277.

Hamzah, Haryani, and Wong Fook Fei. "Miscommunication in Pilot-controller Interaction." 3L: Southeast Asian Journal of English Language Studies 24.4 (2018).

Brumm, Henrik, and Sue Anne Zollinger, "The evolution of the Lombard effect: 100 years of psychoacoustic research," Behaviour 148.11-13 (2011): 1173-1198.

Murray, Iain R., Chris Baber, and Allan South, "Towards a definition and working model of stress and its effects on speech," Speech Communication 20.1-2 (1996): 3-12.

Luo, Jinhong, et al., "The Lombard Effect: From Acoustics to Neural Mechanisms," Trends in Neuroscience, Dec. 2018, vol. 41, No. 12; available at: https:// doi.org/10.1016/j.tins.2018.07.011.

* cited by examiner

- -Pilot Recording Selection GUI- -

Pilot Name: John Doe

Aircraft Type: Boeing 737

Pilot Recordings: LOW STRESS                    106

| | Date | Recording Title |
|---|---|---|
| [X] | 6-12-2022 | "A/C on ground prior to engine start" |
| [ ] | 6-12-2022 | "Engine Start Communication between" |
| [ ] | 5-20-2022 | "After Landing, Rotors Idled" |

⋮

Accept

Pilot Recordings: HIGH STRESS                    105

| | Date | Recording Title |
|---|---|---|
| [X] | 2-17-2021 | "Severe turbulence at Flight level 45" |
| [X] | 7-13-2019 | "Thunderstorms- Flight over Anvil" |
| [X] | 1-25-2017 | "Engine Fire and Failure" |

⋮

Accept

Figure 1B:
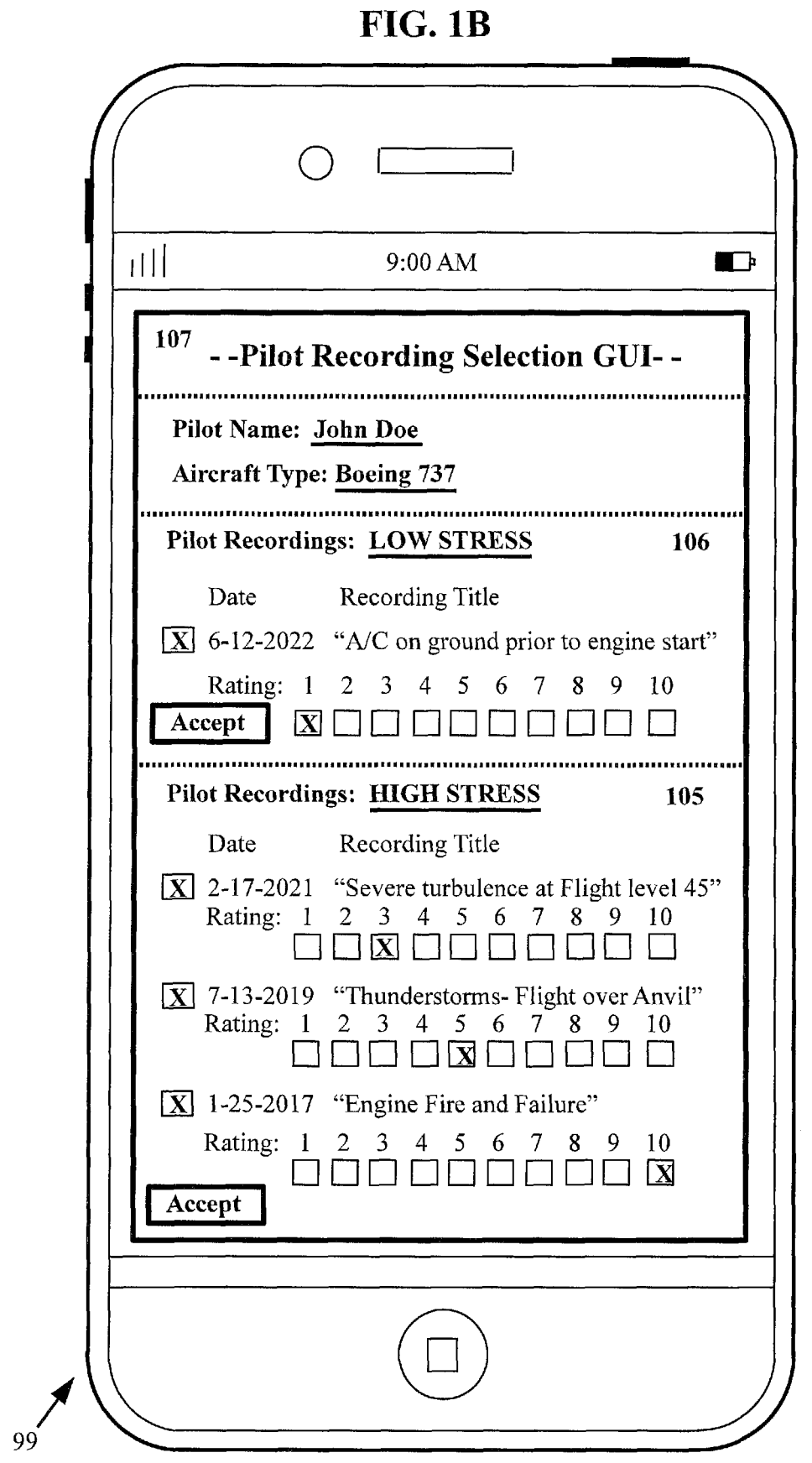

107 --Pilot Recording Selection GUI- -

Pilot Name: <u>John Doe</u>

Aircraft Type: <u>Boeing 737</u>

Pilot Recordings: <u>LOW STRESS</u>                              106

Date            Recording Title

[X] 6-12-2022   "A/C on ground prior to engine start"

Rating:   1    2    3    4    5    6    7    8    9    10

| Accept | [X] | ☐ | ☐ | ☐ | ☐ | ☐ | ☐ | ☐ | ☐ | ☐ |

Pilot Recordings: <u>HIGH STRESS</u>                            105

Date            Recording Title

[X] 2-17-2021   "Severe turbulence at Flight level 45"
Rating:   1    2    3    4    5    6    7    8    9    10
          ☐    ☐   [X]  ☐    ☐    ☐    ☐    ☐    ☐    ☐

[X] 7-13-2019   "Thunderstorms- Flight over Anvil"
Rating:   1    2    3    4    5    6    7    8    9    10
          ☐    ☐    ☐    ☐   [X]  ☐    ☐    ☐    ☐    ☐

[X] 1-25-2017   "Engine Fire and Failure"
Rating:   1    2    3    4    5    6    7    8    9    10
          ☐    ☐    ☐    ☐    ☐    ☐    ☐    ☐    ☐   [X]

| Accept |

99

(Speech and Stress in the context of a Variety of Influences)

(MFCC Algorithm)

SYSTEM FOR DETECTING MICROPHONE COMMUNICATIONS MADE UNDER STRESS, AND FOR MITIGATING PROPAGATION OF STRESSED VOICE COMMUNICATIONS

CROSS-REFERENCES

This application claims priority on U.S. Provisional Patent Application Ser. No. 63/421,691, filed on Nov. 2, 2022, the disclosures of which are incorporated herein by reference.

FIELD OF THE INVENTION

The subject technology relates generally to improving communications by commercial and military pilots to reduce accidents and fatalities, and more particularly relates to a system and method of detecting stress in pilot communications and of manipulating the communications to help reduce or eliminate communication errors that may lead to accidents.

BACKGROUND OF THE INVENTION

Studies have shown that stressful conditions increase the likelihood of aircraft accidents. It has been found that "[a]ttention and working memory are crucial resources for managing situations that involve novelty, difficulty or danger," and that the "stress induced impairments of cognitive functioning . . . help explain errors such as poor management of competing tasks." See, "Effects of Acute Stress on Aircrew Performance: Literature Review and Analysis of Operational Aspects," Dismukes, R., Timothy E. Goldsmith, and Janeen A. Kochan, Appendix B, p. B1, "Stress and Flightcrew Performance: Types of Errors Occurring in Airline Accidents," NASA/TM-2015-218930, 2015.

In particular, errors and accidents tend to occur at a higher rate as a result of the stress of a non-normal situation, as pilots will then have a tendency toward "inadequate or improper communication," in which pilot communication may be incomplete or not sufficiently explicit, or is otherwise degraded in some manner such that one or both pilots fail to understand a critical verbal communication (see, NASA/TM-2015-218930: p. B21).

Impairment of pilot communication resulting in accidents and fatalities is common to commercial air travel and military missions as well.

During stressful situations, pilot communications may be hurried and may become far less effective, a problem that is detected and addressed by the system disclosed herein.

Studies have found that speech under stress becomes distorted, which may have a substantial adverse effect on speech recognition accuracy. See, "Voice Stress Detection," Vijay P. Patil, Krishna Kant Nayak, and Manish Saxena, *International Journal of Electrical, Electronics and Computer Engineering,* 148-154 (2013); "Recognition of Speech Under Stress and in Noise," P. Rajasekaran, G. Doddington, and Joseph Picone, ICASSP'86. *IEEE International Conference on Acoustics, Speech, and Signal Processing,* Vol. 11, IEEE, 1986; and SONDHI, SAVITA, et al., "Vocal Indicators of Emotional Stress," *International Journal of Computer Applications,* 38-43 (2015); Raul Femandez and Rosalind W. Picard, "Modeling Drivers' Speech Under Stress," *Speech Communication,* 145-159 (2003); and "Individual Differences in Human Voice Pitch are Preserved from Speech to Screams, Roars and Pain Cries," Pisanski, Katarzyna, Jordan Raine, and David Reby, *Royal Society open science,* 191642 (2020).

Stress experienced by pilots, as with all people, may be a feeling of emotional tension or physical tension, occurring as a result of a situation that may create anger, frustration, and/or nervousness. See, Murray, I. R., Baber, C., and South, A., "Towards a Definition and Working Model of Stress and its Effects on Speech," Speech Communication, 1996, 20(1-2):3-12; and Hansen, J., Swail, C., South, A., Moore, R., Steeneken, H., Cupples, E., Anderson, T., Vloeberghs, C., Trancoso, I., and Verlinde, P., "The Impact of Speech under 'Stress' on Military Speech Technology," Technical Report AC/323(IST)TP/5 IST/TG-01, NATO Research & Technology Organization RTO-TR-10, 2000.

Many factors may contribute to pilot stress, including, but not limited to: an excessive or unusual/unexpected workload (e.g., the bird strike scenario of US Airways Flight 1549, ultimately termed the "Miracle on the Hudson"), emotions due to personal experiences, environmental influences (turbulence, thunderstorms, etc.), all of which may be categorized as physiological stressors, psychological stressors, and environmental stressors. See also, FIG. 2, which is derived from page 6 of "Evaluation of the Human Voice for Indications of Workload-Induced Stress in the Aviation Environment," Martin Hagmüller, Erhard Rank, and Gernot Kubin, *EEC Note* 18.06 (2006).

A pilot may exhibit measurable symptoms that could be indicative of him/her experiencing stress, such as increased heart rate, but which are not necessarily attributable to a stressful situation, and may instead be due to something positive that caused the pilot to feel excited, e.g., receiving good news from a co-worker such as from an on-board flight attendant or via radio communications.

However, there are ways of measuring a stress response of an individual using physiological signals, including, but not limited to: determination of elevated blood pressure (BP); using an electroencephalogram (EEG) to identify brain signal activity that occurs when the individual is stressed; using galvanic skin response (GSR) apparatus to measure the skin conductance of the individual, as research indicates that stress results in increased skin conductance; and using thermal imaging of the face to detect temperature changes. But such methods are not conducive for making a real-time determination of stress experienced by a pilot flying various different flights, possibly using different aircraft on the same day.

In addition to the above physiological signals that may be acquired, stress can also be identified through speech, which may be more easily obtained for both commercial pilots and military pilots, as it may be determined in a contact-free manner, and without the use of any intrusive devices, e.g., without the use of cameras that would be needed to acquire facial data to detect temperature changes to determine stress.

However, in the past, it was deemed "difficult to understand the separation of research on stress and on emotion recognition," even though "several investigations in emotion recognition may . . . be directly applicable to stress recognition," and each "can be identified . . . by the utilization of similar features (fundamental frequency, jitter, glottal vs. noise excitation, etc.) and by the possibly direct linking between the arousal dimension and stress." See, "Evaluation of the Human Voice for Indications of Workload-Induced Stress in the Aviation Environment," Hagmüller, Martin, Erhard Rank, and Gernot Kubin, *EEC Note* 18.06, p. 10, 2006.

The herein disclosed apparatus and method may use a different approach for determining pilot stress, and may also go further by also operating to alter subsequent communications after the detection of stress in a pilot, in order to improve intelligibility and minimize propagation of the effects of pilot stress. The need for clear and effective communication is vital, and is shown by the numerous fatalities resulting from, for example, miscommunication between pilots and air traffic controllers. See e.g., "Fatal Consequences of Miscommunication between Pilots and Air Traffic Controllers," A. Patty, The Sydney Morning Herald, Oct. 2, 2016.

Devices/methods that may be related, may be shown by the following U.S. Pat. Nos. and Patent Application publication Nos.: U.S. Pat. No. 5,507,291 to Stirbl; U.S. Pat. No. 6,151,571 to Petrushin; U.S. Pat. No. 7,340,393 to Mitsuyoshi; U.S. Pat. No. 7,580,512 to Batni; U.S. Pat. No. 7,912,720 to Hakkani-Tur; U.S. Pat. No. 8,078,470 to Levanon; U.S. Pat. No. 8,204,747 to Kato; U.S. Pat. No. 8,965,770 to Pertrushin; U.S. Pat. No. 9,020,822 to Kalinli-Akbacak; U.S. Pat. No. 9,031,293 to Kalinli-Akbacak; U.S. Pat. No. 9,070,357 to Kennedy; U.S. Pat. No. 9,149,236 to Chun; U.S. Pat. No. 9,418,390 to Chun; 1,009,6319 to Jin; U.S. Pat. No. 10,204,642 to Levanon; U.S. Pat. No. 10,276, 188 to Feast; U.S. Pat. No. 10,453,453 to Penilla; U.S. Pat. No. 10,496,947 to Shaburov; U.S. Pat. No. 10,599,917 to Shaburov; U.S. Pat. No. 10,734,103 to Kaneko; U.S. Pat. No. 10,783,890 to Visser; 10,796,176 to el Kaliouby; 2003/ 0028384A1 Kemp; 2006/0149428A1 Kim; 2007/ 0167689A1 Ramadas; 2008/0091515A1 Thieber; 2013/ 0143185A1 Liu; 2016/0196836A1 Yu; 2020/0058208A1 Ogaz; 2021/0390973A1 Raikar; as well as: CN101420665A; CN101789990A; CN106570496A; CN109274819A; CN111755027A; EP3392884A1; JP4456537B2; JP5394118B2; JP2007041988A; JP2013072979A; JP2022528691A; TWI221574B; WO2010148141A2; and WO2020135194A1.

It is noted that the citing of any reference within this disclosure, i.e., any patents, published patent applications, and non-patent literature, is not an admission regarding a determination as to its availability as prior art with respect to the herein disclosed and claimed method/apparatus.

OBJECTS OF THE INVENTION

It is an object of the invention to provide apparatus and/or a method to improve pilot communications for military and commercial aircraft pilots.

It is another object of the invention to provide apparatus and/or a method that assists in providing clear pilot communications for military and commercial aircraft pilots.

It is a further object of the invention to provide apparatus that may identify a pilot's normal speaking voice and identify when there is stress in a pilot's speech.

It is another object of the invention to provide a system that makes spoken communication easier to understand.

It is also an object of the invention to provide a system that slows down audio communications for pilots when they are under stress.

It is another object of the invention to provide apparatus and/or a method that utilizes deep learning models for stress detection.

It is also an object of the invention to provide a system for prioritizing various pilot-related communications for commercial pilots and military pilots, as being a low priority or a high priority communication.

It is another object of the invention to provide a system permitting pilots to establish a communication plan in which pilot-related communications are prioritized according to a customized hierarchy set by the pilot.

It is also an object of the invention to provide a system configured to detect stress based on a pilot's breathing sounds.

It is another object of the invention to provide a system that operates to alter subsequent communications after the detection of stress in a pilot to improve intelligibility and minimize propagation of the effects of pilot stress.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In a first embodiment, a system is configured to improve pilot voice communication, and includes: a microphone configured to capture speech of a pilot during operational use of an aircraft and to transmit the captured speech; and an audio subsystem. The audio subsystem includes: apparatus configured to store a plurality of recordings of the captured speech of the pilot by the microphone during multiple different periods of the operational use of the aircraft; a pilot recording selection graphic user interface; and a training algorithm. The pilot recording selection graphic user interface may permit selection by the pilot of one or more recordings made during a low stress period of the operational use of the aircraft by the pilot, and may further permit selection by the pilot of one or more recordings made during a high stress period of the operational use of the aircraft. The training algorithm is configured to analyze characteristics of each of the selected one or more recordings made during the low stress period of operational use of the aircraft by the pilot to determine base level of speech characteristics of the pilot during the low stress period. The speech characteristics may include, but is not limited to, one or more of: pitch, and volume. The training algorithm is configured to analyze real-time speech of the pilot, such that when the real-time speech comprises characteristics being increased by a threshold amount over the baseline characteristics, the training algorithm is configured to classify the analyzed real-time speech as being speech made under stress. The audio system is further configured to alter and improve the analyzed real-time speech made under stress, by converting the analyzed real-time speech made under stress to a normal voice tone, using one or more of: an altered pitch, being altered to a pitch when not under stress; a slowed speed, being slowed to a speed when not under stress; and a reduction of staccato. The the system may be configured to alter the analyzed real-time speech made under stress to a normal speech using a phase vocoder.

In a second embodiment, an application utilizes artificial intelligence/machine learning (AI/ML) to determine stress levels from speech patterns and breath sounds received from microphone recordings of individuals under stress. The application then utilizes the detection of stress to trigger a processing function to alter a received verbal communication by slowing it down (or speeding it up) without changing the original pitch of the audio contained therein. In addition, the audio communications of the individual under stress received by the microphone would be "de-stressed" to minimize propagation of stress to others, and increase the intelligibility of the transmitted voice.

The application may be used across many different product lines and for all intercom systems, including, but not limited to, a pilot intercom system. Being able to use an existing intercom system as an operator sensor (e.g., a pilot sensor) provides a secondary function to the normal primary intercom functionality, and may be utilized to provide another measure of the operator's current emotional state, without adding additional hardware to the system. In this embodiment, the capability may be implemented as a software upgrade.

Note that either embodiment may also be used to detect hypoxia in pilots.

BRIEF DESCRIPTION OF DRAWINGS

The description of the various example embodiments is explained in conjunction with the following appended drawings.

FIG. 1 is a flow chart illustrating aspects of an audio subsystem and an asset prioritization system in accordance with at least one embodiment of the herein disclosed system and method.

FIG. 1A illustrates a pilot recording selection graphic user interface that is accessed and being utilized on a smartphone of the pilot, to select particular pilot recordings.

FIG. 1B illustrates a second screen of the pilot recording selection graphic user interface of FIG. 1A, which is being utilized to rate stress levels of a selected pilot recordings.

DETAILED DESCRIPTION OF THE INVENTION

Figure 2:
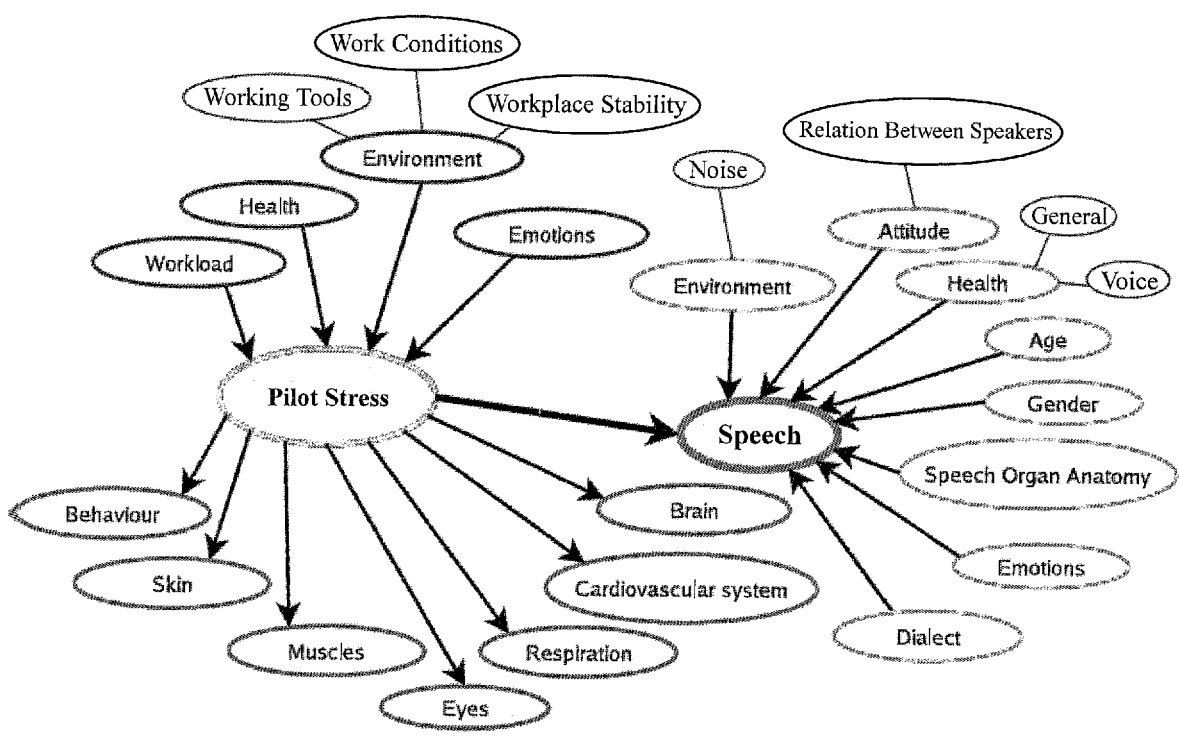
FIG. 2 is a chart illustrating a variety of influences that affect speech and stress.

As used throughout this specification, the word "may" is used in a permissive sense (i.e., meaning having the potential to, or being optional), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that the citing of any reference within this disclosure, i.e., any patents, published patent applications, and non-patent literature, is not an admission regarding a determination as to its availability as prior art with respect to the herein disclosed and claimed apparatus/method.

Furthermore, any reference made throughout this specification to "one embodiment" or "an embodiment" means that a particular feature, structure or characteristic described in connection therewith is included in at least that one particular embodiment. Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value or recitation modified by a term such as "about" or "substantially" is not to be limited to the precise theoretical characteristic or value specified, and may include values that differ from the specified value in accordance with design variations that may be described in the specification, as well as applicable case law. Also, in at least some instances, a numerical difference provided by the approximating language may correspond to the precision of an instrument that may be used for measuring the value or characteristic (e.g., recitation of being "substantially straight"). A numerical difference provided by the approximating language may also correspond to a manufacturing tolerance associated with production of the aspect/feature being quantified/described (see e.g., *Ex Parte Ollmar*, Appeal No. 2014-006128 (PTAB 2016)). Furthermore, a numerical difference provided by the approximating language may also correspond to an overall tolerance for the aspect/feature that may be derived from variations resulting from a stack up (i.e., the sum) of a multiplicity of such individual tolerances.

Stressful conditions increase the likelihood of aircraft accidents, in part due to an increased tendency toward "inadequate or improper communication," in which pilot communication may be incomplete or not sufficiently explicit, or is otherwise degraded in some manner such that one or both pilots or another person fails to understand a critical verbal communication. Stress may hinder the pilot's ability to interpret verbal communication. When under stress, the pilot's ability to process information is diminished, and he/she is also more likely to become distracted. This may lead to mishearing, and to repetition of information, which may be particularly dangerous for military pilots during time-critical mission events.

Impairment of pilot communication resulting in accidents and fatalities is common to both commercial air travel and military missions as well. During stressful situations, pilot communications may be hurried and become far less effective. Therefore the system disclosed hereinafter is configured to detect stress based on a pilot's speech and/or his/her breathing sounds, and the system may also be also further configured to operate to alter subsequent pilot communications to improve intelligibility and minimize propagation of the effects of pilot stress.

The herein disclosed system 100 can be utilized on an aircraft, and may constitute independent equipment added to the aircraft, and/or may even be part of (i.e., be incorporated into) a heads-up display and/or other cockpit equipment, and may alternatively or additionally be located at a ground station or independent ground equipment.

Figure 1:
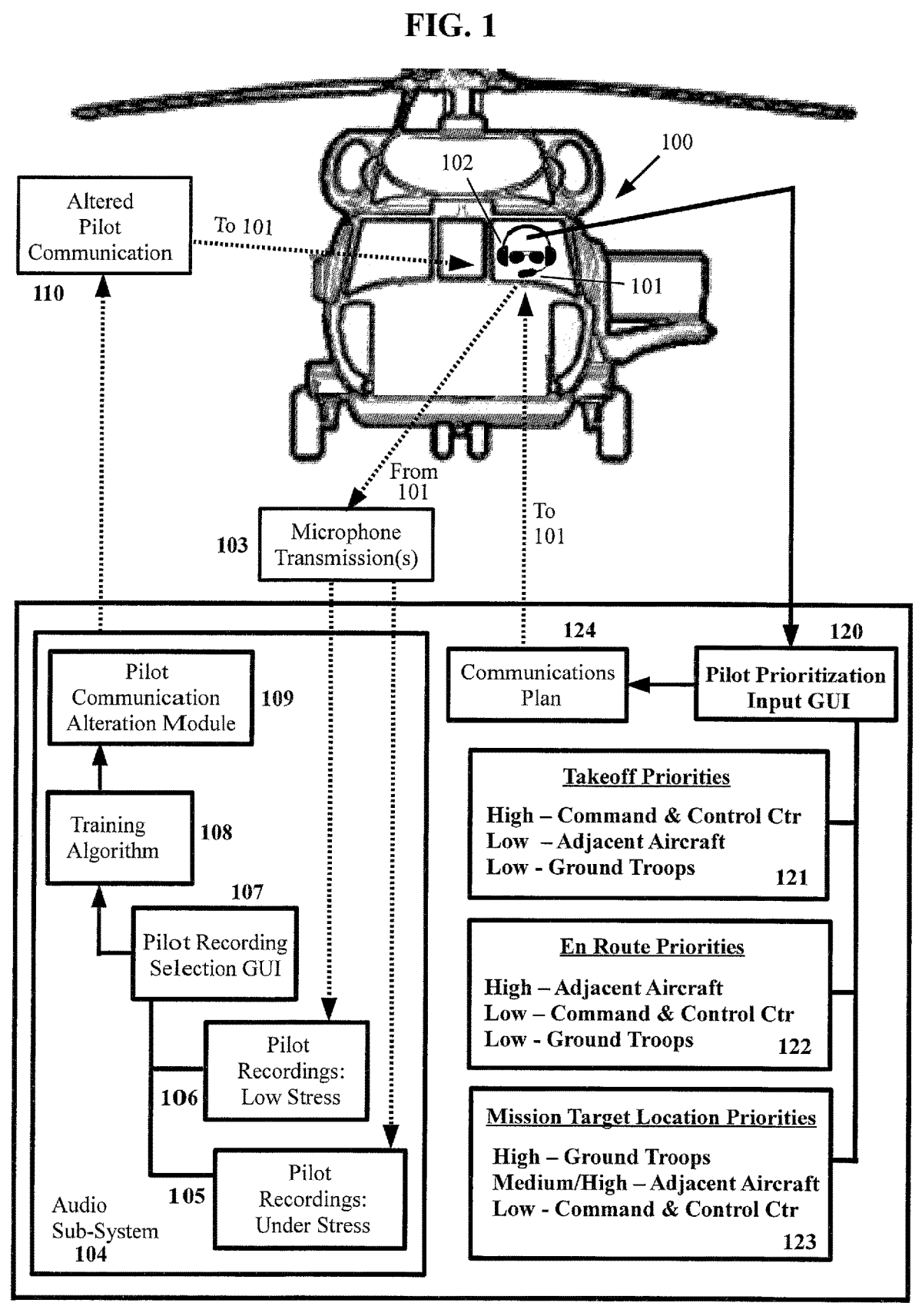

As seen in FIG. 1, the system 100 may include a microphone 101. In one embodiment, the microphone 101 may be an independent microphone that is positioned adjacent to the pilot's mouth, and which is configured to receive and to transmit his/her sounds (speech and/or breathing sounds) directly into the system 100, either through a wired or a wireless connection. In another embodiment, the microphone 101 may be part of the headset 102 that is ordinarily worn by the pilot for transmitting voice communications with air traffic controllers, with pilots of other aircraft, and/or with ground troops.

The sounds emitted by the pilot or pilots immediately during aircraft operations—i.e., speech and/or breathing sounds—may be transmitted by the microphone 101 into an audio subsystem 105, which is particularly configured to detect pilot stress based on either of those two sound categories.

In order to accomplish the detection of stress in the speech of the aircraft's pilot(s) during a commercial flight or a military mission, the system 100 will initially determine a pilot's normal speaking voice and/or breathing sounds. The system 100 may use Artificial Intelligence and Machine Learning to determine both normal pilot speech and stressed pilot speech. A deep learning process may be used to train the system with respect to the speech of pilots, such as when they are subject to minimum stress.

The system 100 may acquire a pilot's normal speaking voice and/or breathing sounds from one or more of several different time periods, including, but not limited to, when the aircraft is on the ground prior to engine start, and/or during an engine start with rotors idle, and/or after a landing with rotors idled, and and/or during engine shutdown. In addition, other known low stress events can be added to the training process (e.g., voice recording from when the pilot contacts ground control for a proposed taxi time for an on-time flight departure). Recordings of many different pilots at these low-stress times may be obtained and stored in database 106 so that the system may recognize the pilot's normal speech and/or breathing sounds. Recordings may be made at these low-stress times at many different airports around the country, and/or around the world, for many different flights, and for one or more different types of aircraft (e.g., commercial aircraft-Airbus A320, Boeing 737, Bombardier CRJ200, Embraer E175 . . . ; and/or general aviation aircraft-Cessna 172, Piper PA-28, Beechcraft Bonanza, Mooney M20 . . . ). Additionally, or alternatively, for a higher degree of accuracy, the recordings and training of the system may be independently made for, and directed to, active commercial pilots, and may also be independently made for, and directed to, active military pilots. Additionally, or alternatively, the recordings and training of the system may also be particularly obtained from and only directed to each individual pilot, as his/her recordings may best be indicative of when he/she is not under stress and when he/she is experiencing a stressful flight situation.

The determination of what constitutes "normal" speech (where the pilot is not under stress) may be made solely by the system 100. Additionally or alternatively, the determination of what constitutes "normal" speech may be made by the user community (i.e., by each individual pilots), in which he/she may toggle GUI button 107 to initiate making one or more speech recordings that may be stored in database 106, based on an individual determination by that pilot of the situation where he/she specifically considered himself/herself to be under low stress and/or in a low stress environment (e.g., at engine start-up).

The GUI button 107 may be part of the cockpit equipment (e.g., part of a heads-up display), or alternatively, a software application may be configured to run on a portable electronic device (e.g., a smart phone 99) which may be downloaded, or on the aircraft's flight computer (electronic control system), and which may be accessed by the pilot, as seen in FIG. 1A. As seen therein, the pilot may utilize a recording selection graphic user interface (GUI) to select particular pilot recordings for input into the training algorithm 108. When a particular recording is selected, as indicated in FIG. 1A by the "X" mark, it may automatically trigger a playback of the recording, permitting the pilot to compare each of those recordings, and to select the ones he/she considers to be most representative of a low stress time period or event. One or more of the recordings can be selected, and after all the desired recording have been selected, the "accept" button may be toggled to input them into the training algorithm 108. Next, as seen in FIG. 1B, a subsequent, second screen of the pilot recording selection GUI may be utilized by the pilot in another embodiment to rate stress levels of each of the selected pilot recordings, which ratings may then be accepted and may be utilized by the system 100.

The pilot community may also determine stress uses cases and the corresponding recordings that may also be used to train the system 100. To do so, the system 100 may record and maintain a database 105 of many or even all communications of each pilot over a long period of time (e.g., an indefinite period, to continuously improve the learning by the system), and the pilot may review the recordings (e.g., periodically, such as after each flight, to continuously improve the learning by the system) using the Pilot Recording Selection GUI 107 to select speech made by the pilot during a period when he/she was in a stressful situation, e.g., high turbulence, thunderstorms, engine fire/failure, and/or flying in adverse weather conditions with/for VIP passengers while being pressured to meet a schedule, such as the Kobe Bryant helicopter crash in the Santa Monica Mountains in 2020, and the John F. Kennedy, Jr. general aviation plane crash near Martha's Vineyard in 1999.

It is noted that the system 100 may make and utilize its own recordings, and/or, the system recordings from the aircraft's cockpit voice recorder may additionally or alternatively be accessed and utilized, particularly for instances of an aircraft incident/accident being investigated by the NTSB.

The determination of what constitutes "stressed" speech may thus be made by the pilot, in which he/she may toggle GUI button 107 to cause intake into the training algorithm 108, of one or more selected speech recordings based on an individual determination by that pilot of the situation where he/she specifically considered himself/herself to be under stress and/or in a high stress environment.

It is noted that this series of continuous recordings made over the extent of each and every flight by the pilot may also be reviewed and utilized by that pilot for selection and entry into the training algorithm 108 of recordings in which he/she specifically considered himself/herself to be under low stress.

The training algorithm of the system 100 may thus be trained to determine the difference between that pilot's speech when the pilot is not stressed and speech when the pilot is under stress. A threshold will be determined by the algorithm as to the base level speech (i.e., the selected non-stressed speech), and the algorithm will be trained to take a "difference" from those base level speech characteristics to be able to recognize speech when the pilot is stressed, using audible measures including, but not limited to, pitch, and/or volume, and/or other components that may also be characteristic of the "Lombard effect." (See e.g., Brumm, Henrik, and Sue Anne Zollinger. "The Evolution of the Lombard Effect: 100 Years of Psychoacoustic Research," *Behaviour* 148.11-13 (2011): 1173-1198; Luo, Jinhong, Steffen R. Hage, and Cynthia F. Moss, "The Lombard Effect: from Acoustics to Neural Mechanisms," *Trends in Neurosciences,* 41.12 (2018): 938-949; and Lane, Harlan, and Bernard Tranel, "The Lombard Sign and the Role of Hearing in Speech," *Journal of Speech and Hearing Research,* 14.4 (1971): 677-709).

The learning may be customized for each individual pilot whereby the difference from the base level speech based on those audible measures is compared to the same audible measures for the recordings when that pilot was under stress.

Therefore, in accordance with one embodiment of the herein disclosed system, a period of speech by a pilot-either a pilot in command (PIC) or a second in command pilot (SIC)-during real-time operation of the aircraft that is thereafter analyzed by the training algorithm 108 and found to exhibit characteristics (e.g., pitch, volume, etc.) being increased by a threshold amount over the baseline characteristics, would constitute speech made under stress. Note that real-time operation of the aircraft need not only be when the aircraft is airborne, and as utilized herein, real-time operation may include any other pilot-related aspect of aircraft operational procedures, including, but not limited to, performing a pre-flight checklist, waiting as the aircraft undergoes a de-icing procedure, etc.

Figure 4:
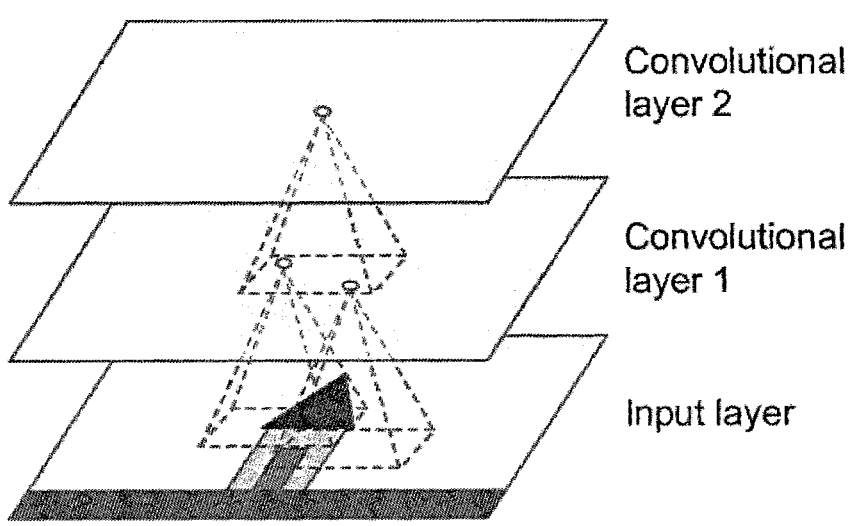
FIG. 4 is an image showing different layers each of which contain image portions that are connected to different parts of an original image, representing different neurons of a convolutional neural network that pick up on different regions of an image.

One machine learning technique that may be utilized as part of the herein disclosed Training Algorithm 108, which is discussed in detail below with respect to the audio preprocessing pipeline of FIG. 6, may be through the use of convolutional neural networks (CNNs), which are inspired by the architecture of the visual cortex in biological systems. A CNN is a deep learning algorithm that specializes in processing digital images as a form of binary representation of visual data. Each neuron in a CNN processes pixels in image only in its receptive field just like how neurons in the brain respond to stimuli in a limited region of the visual field. With multiple neurons picking up on different regions of an image, these neurons can overlap together to form the whole image. This is shown in the image in FIG. 4, where each layer is connected to different parts of the original image.

Figure 5:
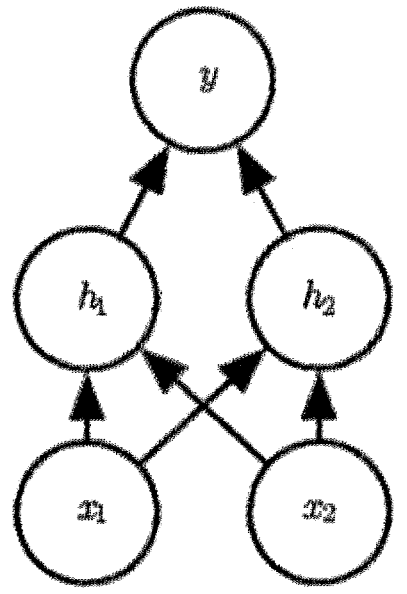
FIG. 5 is a flowchart illustrative of the complexity of a convolutional neural network in which the width and depth are formed of three layers, where the input layer is made up of two neurons (x1 and x2), the hidden layer is made up of two neurons (h1 and h2), and the output layer is made up of one neuron (y).

The idea of a CNN is to connect multiple layers of neurons in a hierarchical structure, where the neurons of the first input layer are connected to pixels in their receptive field and the neurons of the next layer can assemble the low-level features of the first layer into larger higher level features. The hidden layers that follow will then be able to recognize more features of the image. The complexity of a CNN is determined by the width and depth of its network. In the image shown in FIG. 5, there are three layers: the input layer is made up of neurons x1 and x2, the hidden layer is made up of neurons h1 and h2, and the output layer is the neuron y. The last layer is the output layer that computes the patterns that have been assembled by the previous layers. Therefore, the fundamental building block of a CNN are its layers and the input is an image.

To train the CNN, the Speech Under Simulated and Actual Stress (SUSAS) dataset was first used. SUSAS was originally created for speech recognition with military applications. However, because SUSAS is constrained by the short length of the audio clips and limited vocabulary, its performance was limited. Subsequently, the RAVDESS dataset was used, i.e., the Ryerson Audio-Visual Database of Emotional Speech and Song dataset. RAVDESS consists of 1440 audio files recorded of 24 professional actors (gender balanced with 12 females and 12 males) who each recorded 60 different audio clips. The actors all had neutral North American accents. The emotions covered in the dataset were: neutral, calm, happy, sad, angry, fearful, disgust, and surprise. Current constraints of RAVDESS may include overfitting of the model to the voices of the actors in the dataset. The actors may speak in higher intensities of emotions, which can make it difficult for us to test the application on our own voices.

Figure 3:
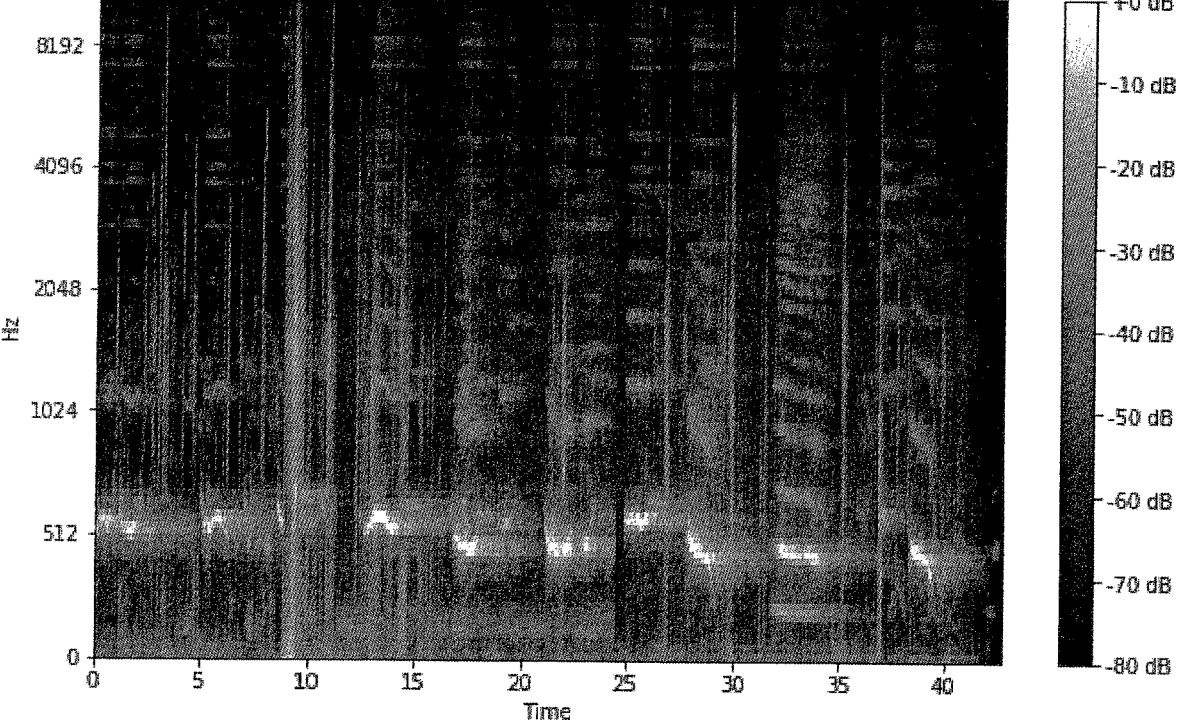
FIG. 3 is an image of a Mel Spectrogram.

The audio preprocessing of FIG. 6 that is discussed below may also utilize a Mel Spectrogram, and example of which is shown in FIG. 3. An understanding of the Mel Spectrogram requires an understanding of how sound is represented. In mathematical terms, a sound wave is a periodic function in time. The sound spectrum of the wave is the set of frequencies making up that signal, which is calculated by the Fourier transform. A frequency representation of the sound spectrum is useful because frequency is related to our perception of pitch. Musical notes are associated with different frequencies. A sound clip is composed of different sound signals at an instantaneous moment in time. Consequently, the spectrum is also a function of time that includes numerous different clips. To capture a change in frequency over time, a spectrogram calculates the spectrum for different windows of the audio clip. The result is a two-dimensional function of frequency and time, with the dependent variable being the amplitude. The amplitude is often in decibels to reflect the human logarithmic perception of sound.

Mel spectrograms can be processed using state of the art computer vision techniques, specifically the convolutional neural network. Neural networks are composed of layers of "neurons" that compute dot products using trainable weights and biases. Each layer looks for different features in the input data. A convolutional neural network is different from regular artificial neural networks by introducing filters. These filters are slid across the image so that the network only looks at a specific part of the image, imitating a receptive field. The Mel Spectrogram may be further processed herein to compute Mel Frequency Cepstral Coefficients (MFCCs), thereby transforming each of the audio clips into data that can be processed using deep learning methods.

Figure 6:
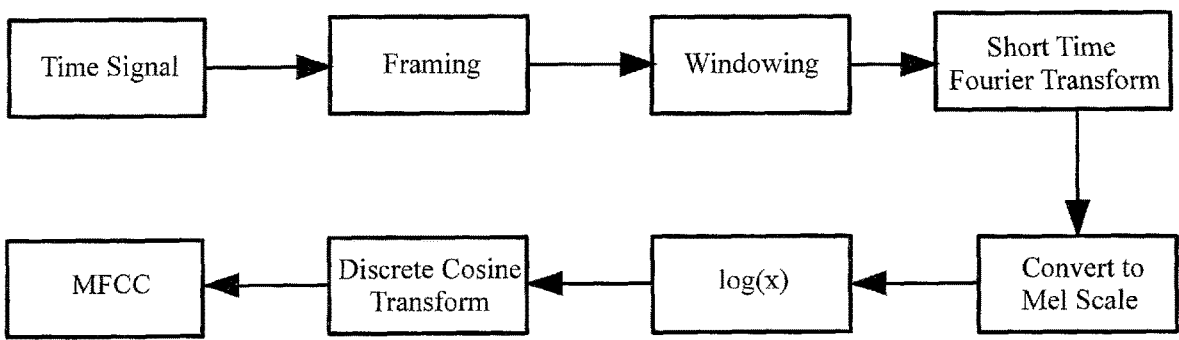
FIG. 6 is a flowchart illustrating steps in a model disclosed herein for converting audio clips in the time domain to Mel frequency cepstrum coefficients.
Figure 7:
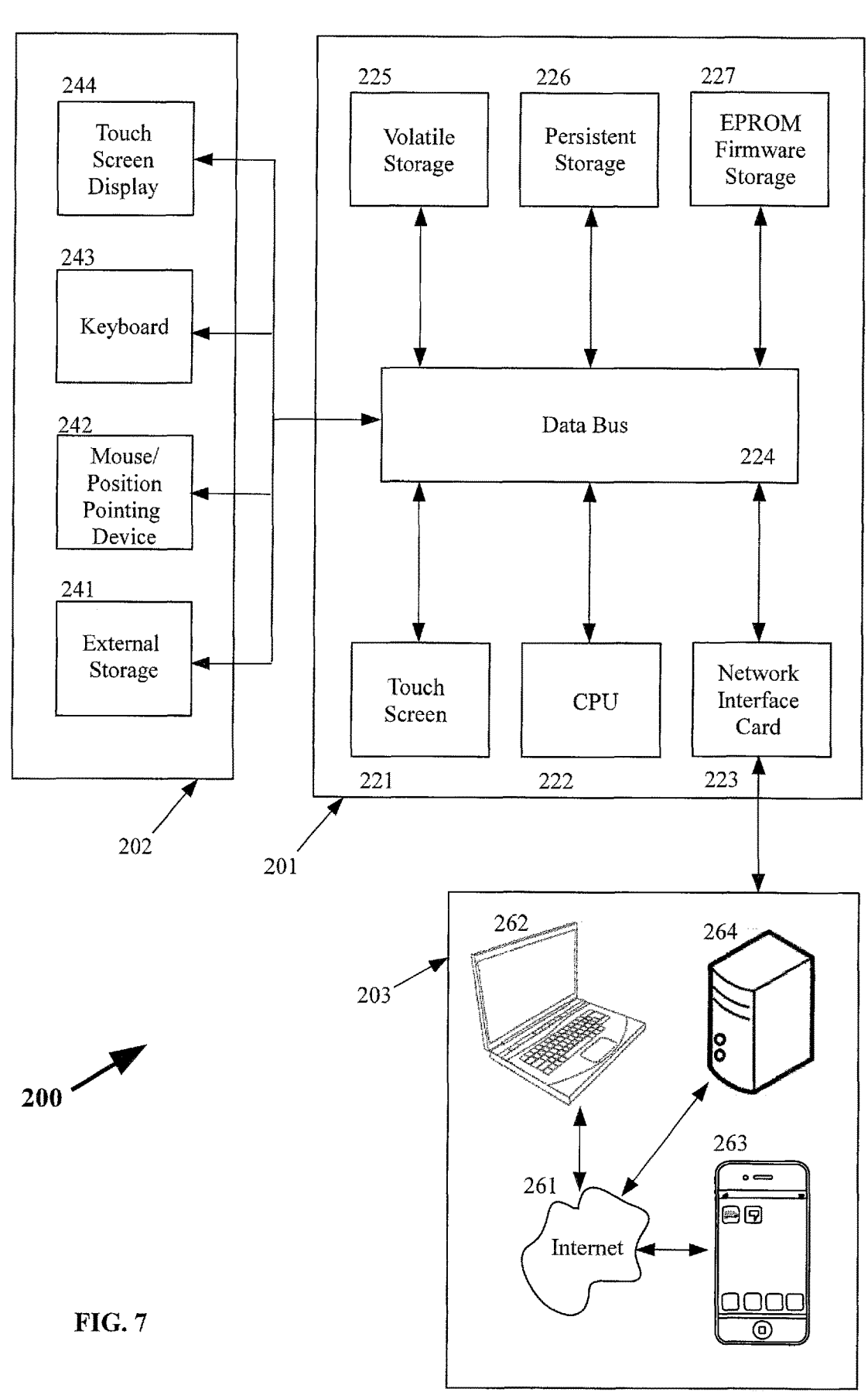
FIG. 7 is a schematic illustration showing an exemplary computing unit capable of being programmed by the instructions of the software of the present invention, and which may include personal computers, cellular phones, and other mobile computing devices.

As noted above, the flowchart of the audio preprocessing pipeline utilized herein is shown in FIG. 6. As discussed above, system 100 may represent an audio file as an "image" representation being in particular the Mel spectrogram. More specifically, system 100 may prepare the data by converting the audio clips in the time domain to Mel Frequency Cepstrum coefficients (MFCCs), which are very suitable for speech recognition because they model the human vocal tract filter and logarithmic perception of sound.

At the first step, system 100 may take the original time signal and zero pad the samples to have a uniform length of 4 seconds, and may also augment the audio by pitch by shifting and adding white noise. Next, system 100 may split the samples into segments by framing. Then, system 100 may apply a windowing function to each segment to produce a desired filtered signal by reducing the amplitude of the discontinuities in the signal. After that, system 100 may apply the short time Fourier transform on the short frames to get the audio signal in the frequency domain. Next, it is converted to the Mel scale, a scale that relates the perceived frequency of a tone to the actual frequency. The Mel scale matches the frequency more closely to what humans hear. Then, system 100 may compute the logarithmic function of the signal, followed by the discrete cosine transform. The MFCCs are obtained as amplitudes of the resulting spectrum. At the last step, the first 12 MFCCs are extracted to focus on the frequency range of the human voice. A convolutional neural network is used to detect stress from the MFCCs. Each pixel from the MFCCs represents 23 ms of speech. By passing filters over 100 ms segments, the model is able to extract higher level features such as phonemes and emotions.

I. Software Configuration

In a further embodiment, the GUI associated with button 107 may also permit the pilot to enter a stress rating, being a rating from 1 to 10, to indicate the level of stress experienced at the time of that particular communication, as perceived by that pilot, with 1 indicating low stress (e.g., for experiencing moderate turbulence, which is not uncommon), 5 indicating moderate stress (e.g., for a flight through a thunderstorm or over the anvil of severe thunderstorms, being accompanied by severe turbulence, which is not common, as thunderstorms are usually avoided), and 10 indicating very high stress (e.g. for an engine fire and/or failure, which is quite rare).

In this embodiment, there may be multiple thresholds for each pilot, each corresponding to one of the entered ratings for a stress level, each of which may be based on a difference between the characteristics of the threshold speech and the characteristics of the stressed speech at each rating; so the system may thus be able to determine not just that the pilot is under stress, but also the level of stress being experience by the pilot.

When the Training Algorithm determines that there is stress in pilot's voice, the system may prioritize the stressed real-time speech of the individual (see FIG. 1), based on the operational scenario, and may minimize information flow. The prioritization may include separating the stressed real-time speech into either a lower priority stressed speech category or a higher priority stressed speech category, based on a current mission stage of that pilot and the intended recipient of the communication. FIG. 1 identifies a matrix of examples of communications being separated in such lower priority and higher priority categories.

The system may operate to delay transmission of the stressed real-time speech having a lower priority, and may transmit the stressed real-time speech having a lower priority at a later time. The system may also include a selectable control panel that may enable a pilot to turn off low priority comms and listen only to high priority communications as needed in a given mission stage/scenario.

The system may operate to alter the stressed real-time higher priority speech and may transmit the altered speech immediately.

To accomplish the alteration, the real-time higher priority speech may be transmitted to the Pilot Communication Alteration Module 109, which may operate to improve its intelligibility, so that the speech is not broadcast in its original stressed form, which may otherwise contribute towards creating/enlarging a stressor environment. This serves to minimize the propagation of stress from one individual to another via the stressed speech.

As such, the Pilot Communication Alteration Module 109 may be configured to alter the analyzed real-time speech prior to transmission of that speech by the aircraft's communication system.

The Pilot Communication Alteration Module 109 may be configured to alter the analyzed real-time speech made under stress, by converting it to a normal, unstressed voice sounds. In one embodiment, the Pilot Communication Alteration Module 109 may be configured to alter the analyzed real-time speech made under stress to a normal voice by altering its pitch, with the pitch being altered to a pitch comparable to when the pilot is not under stress. It is noted that there are many different apects of the pitch of the pilot's speech that may be analyzed and altered in varous embodmients discosed herein, including, but not limited to: pitch contour; jitter, which is short term pitch variations; pitch range; pitch variance; maximum pitch; and the formants (e.g., F1, F2, F3, and F4). In various embodiments, one or more of these may be utilized. In one particular embodiment, mean pitch and maximum pitch may be the only ones used, as some studies have shown that they may be the most indicative feature in speech as to the presence of stress. See e.g., Protopapas, Athanassios, and Philip Lieberman, "Fundamental Frequency of Phonation and Perceived Emotional Stress," *The Journal of the Acoustical Society of America* 101.4 (1997): 2267-2277.

Additionally, or alternatively, the Pilot Communication Alteration Module 109 may be configured to alter the analyzed real-time speech made under stress to a normal voice by slowing the speed of the speech (time stretching), with the speed being altered to a speed comparable to when the pilot is not under stress. Additionally, or alternatively, the Pilot Communication Alteration Module 109 may be configured to alter the analyzed real-time speech made under stress to a normal voice by reducing the staccato of the speech, with the staccato being altered to a staccato comparable to when the pilot is not under stress.

The Pilot Communication Alteration Module 109 may be configured to alter the analyzed real-time speech made under stress as described above through the use of a phase vocoder. The phase vocoder is a technique which can be used to change the speed of audio without altering the pitch. It works by overlap-adding windows of an audio clip and removing subsequent noise.

Applications using the phase vocoder may include separately performing time compression (speeding up audio), time expansion (slowing down audio), and pitch shifting. As used herein, time expansion may be performed using the phase vocoder. The advantage of a phase vocoder is that the result of slowing down audio using the phase vocoder results in less distortions and less change in pitch than if the audio clip had been stretched without such a method.

The method herein by which audio modification is performed using a phase vocoder is given by the following series of steps:

1. Audio in the time domain is broken into multiple overlapping short segments.
2. Each segment is multiplied by a windowing function. This windowing function tends to be bell-shaped and is very commonly a Hamming window.

3. A Short Time Fourier Transform (STFT) is performed on each windowed segment. The output of this is time and frequency representations of the audio segments.

4. Modification is performed on the new time and frequency domains. For example, stretching of the audio signal would occur in this step.

5. Inverse STFT is performed then the segments combined to reconstruct the modified audio in the time domain.

These steps involved in using a phase vocoder may be performed using the Python library librosa.

Initial Testing of Required Software

Initial testing of the software for the invention was run on the laptop and used a microphone for stress detection and audio playback. A requirements.txt file was created that included all libraries needed to run the software. To install the libraries, a virtual environment was first created in the terminal. An Anaconda virtual environment was created by entering the following command in the Anaconda prompt:

conda create-n myenv python=3.8.5

Then, the virtual environment was activated through:

conda create-n myenv python=3.8.5

Follow the instructions outputted by the Anaconda prompt when the commands are entered. A snippet of how the environment is set up is shown in the following image:

☐Anaconda Prompt (anaconda3)
(base)   C:\Users\Evar>conda   create   -n   yourenv   python=3.8.5
Collecting   package   metadata   (current_repodata.json):   done|
Solving environment: failed with repodata from current_repodata.json, will retry with next repodata source.
Collecting package metadta (repodata json): done
Solving environment: done
Package Plan ##
    environment                                        location:
        C:\Users\Evan\anaconda\envy\yourenv
    added/updated specs:
        Python=3.8.5
The following NEW packages will be INSTALLED.
ca-certificates            pkgs/main/win-64::ca-certificates-2022.4.26-haa95532_0
certifi     pkgs     main     win-64::cestif-2021.10.8-py38bas95532_2
operesl pkga/main/win-64:Loperzal-1.1.1n-h2bb1b_0
pip pkgs/main/win-64::pip-21.2.2-py38haa95532_0
python pkgs/main/win-64::python-3.8.5-h5fd99cc_1
setuptools            pkga/main/win-64::setuptools-61.2.0-py38haa95532_0
sqlite pkga/main/win-64::sqlite-3.38.3-h2bb0/1b_0
vc pkgs/main/win-64::vc-14.2-h21ff451_1
va2015_runtime     pkgs/main/win-64::va2015_runtime-14.27.29016-h5e58377_2
wheel pkga/main/noarch::wheel-0.37.1-pyhd3eb1b0_0
wincertstore            pkgs/main/win-64::wincertstore-0.2-py38haa95532_2
Proceed ([y]/n)? y
Preparing transaction: done
Verifying transaction: done
Executing transaction: done

To activate this environment, use

$ conda activate yourenv

To deactivate an active environment, use

$ conda deactivate
(base) C:\Users\Evan>conda activate yourenv
(yourenv) C:\Users\Evan Finally, requirements.txt was used to install the necessary libraries by using the following command:

pip install -r requirements.txt

A snippet of the requirements.txt file is shown below.

☐ requirements.txt—Notepad
File Edit View
This file may be used to create an envronment using:
$ conda create- -name<env>- -file <this file>
platform: win-64
abel-py==1.0.0
alabaster==0.7.12
appdirs==1.4.4
argon2-cifi==21.3.0
argon2-cffi-bindings==21.2.0
asttokens==2.0.5
astumparse==1.6.3
async-generator==1.10
atomicwrites==1.4.0
stas==21.4.0
audioread==2.1.9
babel==2.9.1
backcall==0.2.0
beautifulsoup4==4.10.0
black==22.3.0
bleach==5.0.0
cachetools==5.0.0
certifi==2020.6.20
cffi==1.15.0
charset-normalizer==2.0.12
click==8.1.2
colorama==0.4.4
cario==1.5
cycler==0.11.0
cython==0.29.28
debugpy==1.6.0
decorator==5.1.1
defusedxml==0.7.1
docutils==0.17.1
entrypoints==0.4
executing==0.8.3
fastjsouschema==2.15.3
flatbuffers==2.0
fouttools==4.29.1
gast==0.5.3
google-auth==2.6.0
|

Overall, the application was constrained in the test by the amount of computing power and memory of the device used; however, the laptop was only utilized to develop the software application as a testbed.

Other alternative test arrangements included the possibility of moving the application to the Raspberry Pi. As a much smaller device, the Raspberry Pi would be appropriate to implement in real world settings. However, setting up the software on the Raspberry Pi could require compressing the model, which could negatively affect stress detection accuracy, because in general, the Raspberry Pi has less memory and computing power than a laptop, and such environment constraints could affect the performance of the software.

The main libraries and packages that were used are as follows:

PyAudio
NumPy
Matplotlib Pyplot

Python's time module
Librosa
Tkinter
Tensorflow
Keras from SciPy
Python's playsound module
sounddevice module.

To test the model's performance in stress detection, the software-based testbed streamed audio continuously and made predictions (normal vs stress) in a terminal window. Since CNNs only work with fixed sized inputs, audio was sampled that corresponds to this length (~4 seconds) and inference on this window was performed. To increase the inference speed of the system, windows were overlaped by 2 seconds, so inference is made approximately every 2 seconds. As shown in the image below, at every timestamp recorded, our application determined a confidence level in its prediction.

☐ Anaconda Propmt (anaconda3)-python real_time_up-
   date.py
Current Time: 21:41:12
normal 0.9980183243751526
Current Time: 21:41:16
normal 0.9999961120784064
Current Time: 21:41:16
normal 0.9920661747455597
Current Time: 21:41:18
normal 0.5067818462848663
Current Time: 21:41:20
normal 0.7345990538597107
Current Time: 21:41:22
stress 0.9322516322135925
Current Time: 21:41:24
stress 0.9999955892562866
ENTERING STRESSED MODE
*STRESSED*
Current Time: 21:41:26
stress 0.994368851184845
*STRESSED*
Current Time: 21:41:28
normal 0.9999257796007441

For audio playback, a stress count was implemented that acted as a threshold for the application to enter into "STRESSED" mode. The application enters this mode if two counts of stress are detected in the past 3 predictions. Once the application is in stressed mode, slowed down chunks are played back for 15 seconds until the stress count dissipates. The application was designed to wait 15 seconds for the stressed event to end and revert to normal voice detection. To improve stress detection, the model architecture was changed to test its prediction using the testbed.

Throughout the year, the testing evaluated the system using various datasets. The ideal dataset would contain speech that is easily discernible as stressed or normal, use a large vocabulary, and work well for anyone's voice. Since stress detection is a niche problem, such a dataset does not exist.

As noted above, the testing was started using SUSAS because it was historically the premier dataset for stressed speech recognition. SUSAS contained a vocabulary of 30 words said by 7 actors under neutral, medium stress, and high stress environments. The stress environments involved participants saying the list of words while completing a computer tracking task. We trained models to classify the stress intensity. Our best model achieved an accuracy around 70%.

When the best model was tested with the streaming application, the model detected one of stress or neutral all of the time. Attempts were made to improve the model by recording the inventor's own voices while completing a personal computer tracking task. However, the model still performed poorly on the testbed. The poor performance could be attributed to the low model accuracy, small vocabulary, the small number of participants, and the difficulty of distinguishing the stress environments by our own ears.

Ultimately, a different dataset was sought, despite the fact that there are very few established stressed speech datasets, so emotion datasets were searched. Stressed speech conveys negative emotions such as fear and anxiety. Therefore, the RAVDESS emotional speech dataset was used as a proxy for the task by grouping negative emotions as "stressed speech" and neutral or slightly positive emotions as "normal speech."

RAVDESS contains 24 actors saying 2 sentences two times for 8 emotions at low and high intensities for 1440 clips. The emotions are neutral, calm, happy, sad, angry, fearful, disgust, and surprised. The two sentences deliberately chosen were "The dog is sitting by the door" and "Kids are talking by the door," because they are phonetically balanced.

The conveyed emotions are easily recognized by ear, marking an improvement over SUSAS. However, the dataset suffers from a limited vocabulary and small number of speakers. Additionally, the test environment samples continuous speech, so the audio input to the model does not necessarily start and end with a single sentence. To make the training data better represent the test environment, the dataset was augmented by time and pitch shifting the training data. Time shifting the training data makes some samples begin in the middle of a sentence. Pitch shifting makes the data more robust to different voices.

Finally, the most challenging part of the test was selecting the subset of RAVDESS to choose for the model. The use of disgust and surprised emotions for stress detection made little sense. However, different combinations of the other 6 emotions and intensities were chosen. The subsets that were used re listed below (note that emotion-1 indicates low intensity, emotion-2 indicates high intensity, and neutral speech is only at a single intensity).

| # | Normal | Stressed |
|---|---|---|
| | Subsets: | |
| 1 | neutral, calm-1/2, happy-1/2 | angry-1/2, fearful-1/2, sad-2 |
| 2 | neutral, calm-1, happy-1/2 | angry-2, fearful-1/2, sad-2 |
| 3 | neutral, calm-1, happy-1 | angry-1, fearful-1, sad-1 |
| 4 | neutral, calm-2, happy-2 | angry-2, fateful-2, sad-2 |
| 5 | neutral, calm-1, happy-1 | angry-1, fearful-1/2 |
| 6 | neutral, calm-1, happy-1 | fearful-1/2, sad-2 |
| 7 | neutral, calm-1, happy-2 | fearful-1/2, sad-2 |
| 8 | neutral, happy-1/2 | fearful-1/2, sad-2 |
| 9 | neutral, calm-1 | fearful-2, sad-2 |
| 10 | neutral, happy-1 | fearful-1, sad-2 |
| 11 | neutral, happy-2 | fearful-2, sad-2 |
| 12 | neutral | fearful-1 |
| 13 | neutral | fearful-2 |

The models were trained with each of these subsets and consistently achieved accuracy of greater than 90%. Many subsets were evaluated because of the tradeoff between generalizability and what actually seemed to work well in the testbed utilized. Usually, using more data tends to prevent overfitting because a model would see more examples of stressed speech. However, it was found that the smaller subsets, especially those that used low intensity emotions, seemed to work better on the inventor's voices, which may be because the inventor's voices are generally quiet, even when trying to act/sound stressed, while conversely the professional actors were very expressive for high intensity emotions.

Model Architecture

The test sought to simultaneously train different models with the different training subsets. The architectural decisions for the machine learning models were inspired by an earlier work which found that phonemes can be recognized in less than 100 ms, while the basic emotions of fear, anger, disgust, sadness, and happiness are recognized from 300 to 500 ms. See, Pell, Marc D., and Sonja A. Kotz, "On the time course of vocal emotion recognition," *PLOS One* 6.11 (2011): e27256.

From a raw time signal, the first 12 MFCCs were extracted using a 512-point FFT. Therefore, each value of the MFCC corresponds to 23 milliseconds of speech at a sample rate of 22050 Hz. As there are 12 coefficients and the time signals have been padded to 4 seconds, the shape of the MFCC is (12, 700).

Since the MFCC is much longer in the x dimension than the y dimension, the test first uses 1D convolution to learn temporal features for each coefficient. Since each value of the MFCC corresponds to 23 ms, the test used a 1×5 filter size that has a receptive field of 115 ms for the first 1D convolution to potentially recognize phonemes. The test also used up to 48 filters since English has about 42 phonemes.

The test followed 1D convolution by 1D max pooling with a kernel size of 1×5 to shrink the temporal dimension further. Since the convolution has a stride of 1, the receptive fields overlap, and only the most prominent features need to be kept.

A second convolution layer is used to recognize the emotion. The test used kernel sizes of 1×3 and 1×5, which have receptive fields of approximately 300 ms and 500 ms respectively. This corresponds to the time it takes to recognize emotions in speech. We follow this layer with pooling. After the convolution and pooling, we flatten the output and pass it through one or more dense layers. The final layer uses a sigmoid activation function since the model is trained for binary classification. Variations of this architecture have been tested with different hyperparameters such as the number of filters, kernel sizes, batch size, and learning rate.

Test Results

The test explored the large design space by jointly modifying the training data and the machine learning model and deploying the model to our testbed. All of our models achieved greater than 90% accuracy. It was observed that when less emotions were used from RAVDESS (i.e., a smaller subset), it was possible to achieve accuracy greater than 90% with fewer layers. However, the accuracy on the training data is misleading because it does not necessarily have good performance on the inventor's voices.

The best two models were respectively trained with subset 6, as seen below:

```
model=keras.models.Sequential([keras.layers. Normal-
    ization(axis=1, mean=scaler.mean_, variance=scaler
    var_),
([keras.layers.Normalization (axis=1, men=scaler.mean,
    variance=scaler.var),
keras.layers.Conv1D(16, 5, activation="relu",
    input.shape=mfccs.shape[1:].
    kernal.regularizer=regularizers.12(0.001)),
keras.layers.Maxpooling2D(pool_size=(1,5), strides=
    (1.5), padding='same'),
```

```
keras.layers.Conv1D(8, 3, activation="relu",
    kernal.regularizer=regularizers.12(0.001)).
keras.layers.MaxPooling2D (pool_size=(1, 3), strides=(1,
    3), padding='same'),
keras.layers.Flatten( ),
keras.layers.Dense(4, activation="relu"),
keras.layers.Deuse(1, activation="sigmoid", kernal_regu-
    larizer-regularizers.12(0.001)),
``` and trained with subset 13, as shown below:

```
model=keras.models.Sequential([keras.layers.Normaliza-
    tion(axis=1, mean=scaler.mean_, variance=scaler,
    var_),
keras.layers.Conv1D(4, 5, activation="relu",
    input.shape=mfccs.shape[1:],
    kernal.regularizer=regularizers.12(0.001)),
keras.layers.MaxPooling2d(pool.size=(1,15), strides=
    (1.15), padding='same'),
keras.layers.flatten( ),
keras.layers.Dense(1, activation="sigmoid",
    kernal.regularizer=regularizers.12(0.001)),
```

Overall, the second smaller model worked slightly better in our test environment.

Software to provide the herein disclosed GUI functionality may run on a suitable computing device, such as a server, a tablet, a cell phone, or other mobile smart device, so a description of such an accessorized exemplary computer system is hereinafter disclosed, even though a particular embodiment may not require all of the described components. Exemplary computer system 200 (i.e., a client device associated with a particular user) is shown schematically in FIG. 6, and which may comprise computing unit 201 interacting with external peripherals 202, such as a separate touch screen display 244, and interacting with network resources 203, including use of the internet 261, and other computers (or other client devices or a server), which may be a laptop computer 262 (i.e., a second client device associated with a second user), a smart phone 263 (i.e., a third client device associated with a third user), a server 264, etc.

The computing unit 201 may include a data bus 224 for communicating information across and among various parts of computing unit 201, and a central processing unit, which may be a microprocessor (hereinafter "processor" or "CPU") 222 coupled with a bus 224 for processing information and performing other computational and control tasks. Computing unit 201 may also include a volatile storage 225, such as a random access memory (RAM) or other dynamic storage device, coupled to bus 224 for storing various information as well as instructions to be executed by processor 222. The volatile storage 225 may also be used for storing temporary variables or other intermediate information during execution of instructions by processor 222. Computing unit 201 may further include a read only memory (ROM) or an erasable programmable memory (EPROM) 227 or other static non-transitory storage device coupled to bus 224 for storing static information and instructions for processor 222, such as basic input-output system (BIOS), as well as various system configuration parameters. A persistent storage device or non-volatile memory 226, such as a magnetic disk, optical disk, or solid-state flash memory device may be provided and may be coupled to bus 224 for storing information and instructions.

Computing unit 201 may be coupled via bus 224 to an integral display 221, possibly a touch-screen display, for use in displaying information to a user. If desired, computing unit 201 may be coupled via bus 224 to an external display screen 244. An external input device 243 (e.g., a standard keyboard) may be coupled to bus 224 for communicating information and command selections to processor 222. A cursor control device 242, such as a mouse, a trackball, or cursor direction keys, may be used for communicating direction information and command selections to processor 222 and for controlling cursor movement on display 244. An external storage device 241 may be connected to the computing unit 201 via bus 224 to provide an extra or removable storage capacity for the computing unit 201, which may be used to facilitate exchange of data with other computer systems.

Some of the techniques herein may be performed by computing unit 201 in response to processor 222 executing one or more sequences of one or more instructions contained in the volatile memory 225. Execution of the sequences of instructions contained in a non-transitory memory may cause processor 222 to perform the process steps described herein. In alternative embodiments, specific hard-wired digital circuitry may be used in place of, or in combination with, software instructions to implement the invention.

The term "computer-readable medium" as used herein refers to any medium that participates in providing instructions to processor 222 for execution. The computer-readable medium is just one example of a machine-readable medium, which may carry instructions for implementing any of the methods and/or techniques described herein. Various forms of computer readable media may contain one or more sequences of one or more instructions for the processor 222 to execute, including non-volatile media (storage device 226), and volatile media (storage device 225). Common forms of non-transitory computer-readable media include, for example, a floppy disk, a hard disk, magnetic tape, or any other magnetic medium, a CD-ROM, a flash drive, and a memory card.

The computing unit 201 may thus also include a communication interface, such as network interface card 223 coupled to the data bus 222. Communication interface 223 may provide a two-way data communication coupling to a network link that may be connected to a local network. For example, communication interface 223 may be an integrated services digital network (ISDN) card or a modem to provide a data communication connection to a corresponding type of telephone line, or it may be a local area network interface card (LAN NIC) to provide a data communication connection to a compatible LAN.

Network link 223 also typically provides data communication to other network resources. For example, the network link may provide a connection over the internet 261 to the world-wide-web. Thus, the computing unit 201 can access resources located anywhere using the Internet 261. Also, the computing unit 201 may also be accessed by, or communicate with, other computers (e.g. 262), or another smart device (e.g., smartphone 263), generally with permission, and which may be located anywhere with access to the internet 261.

While illustrative implementations of one or more embodiments of the disclosed system are provided hereinabove, those skilled in the art and having the benefit of the present disclosure will appreciate that further embodiments may be implemented with various changes within the scope of the disclosed system. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

The invention claimed is:

1. A system configured to improve pilot voice communication, said system comprising:
   a microphone, said microphone configured to receive speech of a pilot during operational use of an aircraft and to transmit the received speech; and
   an audio subsystem, said audio subsystem comprising:
      a database configured to store a plurality of recordings of the received speech of the pilot by said microphone during multiple different periods of the operational use of the aircraft;
      a pilot recording selection graphic user interface, said pilot recording selection graphic user interface configured to provide a list of recordings of the pilot that were recorded during operational use of the aircraft by the pilot, and to permit selection by the pilot of one or more recordings made during a low stress period of the operational use of the aircraft by the pilot, and to permit selection by the pilot of one or more recordings made during a high stress period of the operational use of the aircraft;
      a training algorithm, said training algorithm configured to analyze characteristics of each said selected one or more recordings made during the low stress period of operational use of the aircraft by the pilot to determine a base level of speech characteristics of the pilot during the low stress period; said speech characteristics comprising one or more of: pitch, and volume;
      wherein said training algorithm is further configured to analyze real-time speech of the pilot;
      wherein when the real-time speech comprises characteristics being increased by a threshold amount over the baseline characteristics, said training algorithm is configured to classify said analyzed real-time speech as being speech made under stress; and
      wherein said audio system is configured to use machine learning to alter and improve said analyzed real-time speech made under stress by conversion of the analyzed real-time speech made under stress to a normal voice tone by slowing down or speeding up the analyzed real-time speech made under stress without changing the original pitch of the audio contained therein.

2. The system according to claim 1, wherein said system being configured to alter said analyzed real-time speech made under stress comprises: conversion of the analyzed real-time speech made under stress to a normal voice tone.

3. The system according to claim 2, wherein said system is configured to alter said analyzed real-time speech made under stress to a normal voice tone using one or more of:
   an altered pitch, being altered to a pitch when not under stress; and
   a reduction of staccato.

4. The system according to claim 3, wherein said system is configured to alter said analyzed real-time speech made under stress to a normal voice tone using a phase vocoder.

5. The system according to claim 4, wherein said system is configured to alter said analyzed real-time speech prior to transmission by said microphone.

6. The system according to claim 1, wherein said system is configured to improve aircraft pilot voice communication with one or more of a command and control authority, one or more adjacent aircraft, and one or more ground forces.

7. The system according to claim 1, wherein said pilot recording selection graphic user interface is available on any one or more of: a cell phone display; a heads-up display of the aircraft; and a piece of cockpit equipment.

8. The system according to claim 1, wherein said pilot recording selection graphic user interface is further configured to permit the pilot to rate a stress level of each said selected recording, being a rating from one to ten; and wherein each said rated recording is used to train said system.

\* \* \* \* \*